United States Patent

Orr et al.

[11] Patent Number: 4,569,688
[45] Date of Patent: Feb. 11, 1986

[54] N-FORMYL-3-CARBOXYAZETIDINE AND ITS USE FOR STERILIZING THE MALE PARTS OF WHEAT PLANTS

[75] Inventors: Alexander F. Orr, Teynham, Nr. Sittingbourne; David R. Clifford, Sheppey, both of United Kingdom

[73] Assignee: Shell Oil Company, Houston, Tex.

[21] Appl. No.: 597,293

[22] Filed: Apr. 6, 1984

[30] Foreign Application Priority Data

Apr. 13, 1983 [GB] United Kingdom ................ 8310033

[51] Int. Cl.⁴ .................... A01N 43/44; C07D 205/04
[52] U.S. Cl. .................................... 71/88; 260/239 A
[58] Field of Search .................... 260/239 AR; 71/88

[56] References Cited

FOREIGN PATENT DOCUMENTS 029265  6/1981  European Pat. Off. .
2312045  9/1974  Fed. Rep. of Germany .......... 71/88
2136903 12/1972  France .

OTHER PUBLICATIONS

Chen et al., Bull. Chem. Soc. Jpn., vol. 40, (1967), pp. 2398-2404.
Igarashi, Chem. Abstracts, vol. 91, (1979), Abst.: 56800g, 141178e.

Primary Examiner—Donald G. Daus
Assistant Examiner—William A. Teoli, Jr.

[57] ABSTRACT

N-formyl-3-carboxyazetidine of the formula

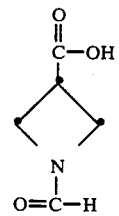

and use thereof for sterilizing the male parts of wheat plants.

3 Claims, No Drawings

N-FORMYL-3-CARBOXYAZETIDINE AND ITS USE FOR STERILIZING THE MALE PARTS OF WHEAT PLANTS

BACKGROUND OF THE INVENTION

To obtain $F_1$ hybrid seeds which have advantages over non-hybrid seeds, seed breeders cross-pollinate carefully selected parent plants. Wheat plants have hermaphroditic flowers, and normally self-pollinate. This characteristic can cause a problem in effecting cross-breeding, leading to mixtures of hybrid and non-hybrid seed. The problem has been solved in the past by emasculating (removing the male anthers) of each of the flowers of the prospective female parent plant by hand before it is pollinated with pollen from the prospective male parent. Such hand operations are extremely laborious and time-consuming, and require highly-skilled workers. Much research is being carried out with a view to effecting the emasculation by treating the prospective female parent with a chemical, and thus avoiding such hand operations.

DESCRIPTION OF THE INVENTION

It now has been found that N-formyl-3-carboxy-azetidine selectively sterilizes the male parts of wheat plants by way of rendering the pollen grains non-functional—i.e., sterile. N-formyl-3-carboxyazetidine is described by the formula

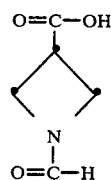

The present invention thus comprises this novel compound, a method for sterilizing the male parts of wheat plants, which method comprises applying to a wheat plant, prior to pollen shed, an effective amount of the compound of Formula I, and a method for producing hybrid wheat seed which comprises applying to the candidate female parent wheat plant prior to pollen shed an effective dosage of a compound of Formula I, causing the candidate female plant to be pollinated with pollen from a candidate male parent wheat plant, allowing the female parent to mature until the seed is mature, and harvesting the seed. The invention also includes compositions adapted for effecting these methods which comprise an effective amount of the compound of Formula I, an inert carrier and a surface-active agent. The method according to the invention generally produces plants in which male sterility has been induced without an unduly adverse effect upon the female fertility of the plants.

It appears that the compound of Formula I has the desired effect when it is applied to the plant at a time during the development of the pollen—i.e., between the time of floral initiation and pollen shed. Preferably, the compound is applied somewhat before the pollen is wholly mature, to ensure movement of an effective dosage of the compound into the concerned plant tissue, believed to be the pollen grains, in time to effect sterilization of the pollen. In wheat, this "application window" extends from a stage of growth between late tillering and emergence of the ear, although it may extend from about growth stage 32 (second stem node detectable; anthers beginning to differentiate) to about growth stage 49 (awns appearing—i.e., late booting; pollen grains well developed). The definitions and meanings of the numbered growth stages are those set out by D. R. Tottman and R. J. Makepeace, Annals of Applied Biology, 93, 221–234 (1979).

The compound of Formula I is suitably applied at a dosage of from 0.05 to 15 kilograms per hectare, dosages of from 0.25 to 2.5 kilograms per hectare ordinarily sufficing.

The present invention also provides a method for producing $F_1$ hybrid seed which comprises cross-pollinating a plant which has been treated with the compound of Formula I, according to the method of this invention, with a second untreated plant.

The compound of Formula I will be formulated for use in the methods of the invention. The invention, therefore, also provides a pollen-sterilizing composition which comprises a compound of Formula I, together with a suitable carrier and a suitable surface-active agent.

The compound of Formula I is conveniently applied as a water solution containing a small amount of an inert surfactant, a nonionic material being suitable for the purpose. The surfactant of course must be a material that is not toxic to the plant to be treated, at the dosage of the azetidine which is to be used. In such compositions, the concentrations of the compound of Formula I suitably is of the order of about 0.01 to about 1 percent by weight of the composition, while the concentration of surfactant is of the order of 0.05 to 2.0 percent (ordinarily about 0.1 to about 1.0 percent), on the same basis.

It is evident from the foregoing that this invention contemplates compositions containing as little as about 0.1% by weight to as much as about 75% by weight of the compound of Formula I as the active ingredient.

The compound of formula I can be prepared by methods described by N. H. Cromwell and B. Phillips in Chemical Reviews, 1979, volume 79, pages 331–358. As shown in Example 1, hereinafter, it can be prepared by treating 3-carboxyazetidine (A. G. Anderson, Jr. and R. Lok, Journal of Organic Chemistry, 1972, volume 37, pages 3953-5) with acetic formic anhydride.

The following example illustrates the invention. In Example 1, the identity of the product was confirmed by appropriate chemical and spectral analyses.

EXAMPLE 1

Preparation of N-formyl-3-carboxyazetidine (1)

(a) 15 g of 1-diphenylmethyl-3-cyanoazetidine (Anderson and Lok) was mixed with 50 ml of 2-methoxyethanol and added to a solution of 13 g of potassium hydroxide in 10 ml of water. The resulting mixture was refluxed for 15 hours, during which time ammonia was evolved, and then poured onto 1500 ml of ice and water. This mixture was then acidified with dilute hydrochloric acid until the pH was 1.5, and was then extracted with dichloromethane. The aqueous phase was adjusted to pH 5 by addition of solid sodium bicarbonate to the stirred solution. 1-Diphenylmethyl-3-carboxyazetidine (1A) separated from the solution as a fine white solid. The solid was collected, washed with water and air-dried. M.p.: 190°–191° C. with decomposition. (b) 10 g of 1A was suspended in 300 ml of methanol, and 6 g of a catalyst of palladium II hydroxide on charcoal, prepared by the method described in Tetrahedron Letters, 1967, page 1663, was added. The mixture was hydrogenated in a Parr apparatus at an initial hydrogen pressure of about 3.5 atmospheres absolute for 3 hours. Uptake of hydrogen stopped abruptly after 1 hour. The solution was filtered and evaporated almost to dryness under reduced pressure. The aqueous residue was extracted several times with dichloromethane and the combined extract phase was evaporated to dryness. The white solid residue was recrystallized from ethanol to give shiny plates of hydrated 3-carboxyazetidine (1B), m.p.: 169°–170° C. with decomposition.

2 g of 1B and 60 ml of acetic formic anhydride were stirred together for 3 hours at room temperature.

Remaining anhydride was evaporated under reduced pressure and the solid residue was dissolved in water. The water was evaporated and the crude product recrystalized from ethanol/ethyl acetate to give 1, as a solid, m.p.: 129°–131° C.

EXAMPLE 2

Demonstration of Pollen-Sterilizing Activity and Selectivity

The capability of Compound 1 to sterilize the pollen of wheat plants, and the capability of the treated wheat plants to set seed by cross-pollination, was assessed as follows:

Plants of spring wheat (*Triticum aestivum* cv. Yecora rojo) were grown in pots (four plants per pot) in a greenhouse under controlled conditions for optimum growth. The compound was applied as an aqueous solution containing 0.75% Tween 20 as surfactant, at the rate of 600 liters per hectare. Control plants were sprayed with water containing 0.75% Tween 20. The compound was applied at dosages of 1 and 2 kilograms per hectare, and was applied to the plants during spike development prior to head emergence. The stage of development (length of spike primordia) was determined by measuring the lengths of a random sampling of five spikes. All were in the range of 3.5 to 4.0 centimeters in length (stages 33–43, Zadok's scale).

Following treatment, the plants were placed in a randomized block arrangement, with at least four replicates per treatment and two controls per replicate.

As the spikes emerged, the mainstem and first tiller of each of the four plants was bagged to prevent cross-pollination. In some cases, half (i.e., two) of the mainstem spikes per pot were hand-crossed with pollen from untreated plants. Control spikes were clipped and hand-crossed.

When the developing seeds reached the soft dough stage, water was withheld, to dry the seeds for harvest, and the number of seeds that had been set were counted. The following results were obtained.

TABLE I

| Compound | Dosage (kg/ha) | Seed Set, Treated Heads | | Seed Set, hand-crossed heads |
|---|---|---|---|---|
| | | Mainstem | Tillers | |
| 1 | 1 | 11.0 ± 9.7[a] | 41.3 ± 7.7[b] | 57.0 ± 13.8 |
| | 2 | 0.8 ± 1.0 | 0 ± 0 | 53.3 ± 8.5 |
| Control | | 72.3 ± 4.4 | 122.5 ± 16.3 | 53.8 ± 4.7 |

[a]Average seed set per two bagged heads, + standard error

Compound 1 has been found to be nonphytotoxic to wheat plants at the dosages required to effect sterilization of the male parts of the plants.

We claim:

1. The compound: N-formyl-3-carboxyazetidine.
2. A method for sterilizing the male parts of a wheat plant, which comprises applying to the plant prior to pollen shed an effective dosage of the compound of claim 1.
3. A method for producing a hybrid wheat seed which comprises applying to a candidate female parent wheat plant prior to pollen shed an effective dosage of the compound of claim 1, causing the candidate female plant to be pollinated with pollen from a candidate male parent plant, allowing the female parent to mature until the seed is mature, and harvesting the seed.

* * * * *